United States Patent [19]

Miller

[11] Patent Number: 4,532,937

[45] Date of Patent: Aug. 6, 1985

[54] SEBUM COLLECTION AND MONITORING MEANS AND METHOD

[75] Inventor: David L. Miller, Dallas, Tex.

[73] Assignee: Cuderm Corporation, Dallas, Tex.

[21] Appl. No.: 555,817

[22] Filed: Nov. 28, 1983

Related U.S. Application Data

[63] Continuation-in-part of Ser. No. 453,836, Dec. 28, 1982, abandoned.

[51] Int. Cl.³ ............................................. A61B 10/00
[52] U.S. Cl. .................................... 128/759; 604/897
[58] Field of Search ............... 128/632, 749, 759, 760, 128/630; 422/56; 436/71; 604/317, 327, 358, 360, 367, 378, 384, 890, 892, 896, 897

[56] References Cited

U.S. PATENT DOCUMENTS

| | | | |
|---|---|---|---|
| 3,426,754 | 2/1969 | Bierenbaum et al. | 604/897 X |
| 3,731,683 | 5/1973 | Zaffaroni | 604/897 |
| 3,906,933 | 9/1975 | Tur et al. | 128/759 |
| 4,073,291 | 2/1978 | Marvel et al. | 604/897 X |
| 4,190,056 | 2/1980 | Tapper et al. | 128/630 |
| 4,190,060 | 2/1980 | Greenleaf et al. | 128/760 |
| 4,224,950 | 9/1980 | Bore et al. | 128/759 |

FOREIGN PATENT DOCUMENTS 90161  6/1982  Japan ..................................... 436/71

OTHER PUBLICATIONS

Shiseido Paper Powder.

*Primary Examiner*—Edward M. Coven
*Attorney, Agent, or Firm*—Irving Newman

[57] ABSTRACT

Means for absorbing sebum screted by sebacious glands of a subject as well as providing semi-quantitative estimation of the rate of sebum production at various sites on the subject's skin and a record of excretion patterns on the skin, said means comprising a microporous hydrophobic polymeric film substrate coated on a major surface with a high molecular weight adhesive that is resistant to migration into the pores of the polymeric film. Said means may also be used to provide therapy by absorbing excess sebum or delivering medication to sites or abnormal sebum secretion. Method for ascertaining secretion patterns on the skin by applying to the skin for a preselected time a microporous, hydrophobic, polymeric film.

15 Claims, No Drawings

SEBUM COLLECTION AND MONITORING MEANS AND METHOD

CROSS-REFERENCE TO RELATED APPLICATIONS

This application is a continuation-in-part of my copending application Ser. No. 453,836, filed Dec. 28, 1982, now abondoned.

TECHNICAL FIELD

The invention relates to means for monitoring the location of sebaceous glands as well as the relative rate of secretion. More particularly, the invention involves the use of a microporous film to ascertain the degree of sebacous gland activity at a skin site. In a preferred embodiment, the invention relates to an adhesive film that can be applied to the skin for absorbing sebum therefrom. After removal, the film contains surface patterns and can be compared to standards for determining the location and relative rate of secretion of sebaceous glands on the subject's skin. The resulting analysis is most helpful in diagnosing acne as well as oily skin in general. In another aspect, the adhesive film can be used therapeutically to reduce the level of sebum on a subject's skin to a desired level, as well as to deliver an active ingredient directly to the site of overproductive or under-productive sebaceous glands.

BACKGROUND ART

Acne vulgaris is a dermatological disorder prevalent in adolescence. It appears most commonly on the face and trunk of the patient. The basic lesion of acne is the comedo (or "blackhead") of a pilosebaceous follicle. In its mildest form, only a few comedones are present, but in more severe forms, many severe, persistent comedones are present. Severe acne can cause permanent scarring.

Acne occurs when there is a filling up of the follicle with a rather tough, keratinous material. These impactions of horny material are the whitehead and blackhead. As a result of bacterial growth in these horny impactions, the follicle may rupture, initiating the inflammatory phase of the disease, which takes the form of pustules, papules, cysts and nodules.

Over the years, there have been a variety of theories regarding the cause, prevention and treatment of acne. Dr. F. Lyons reported at the 1982 annual meeting of the European Society of Dermatological Research the results of a study that shows a direct relationship between excess sebum secretion and acne. This is believed to provide important information for the monitoring and management of acne, and a great impetus for studies of the secretion patterns of sebaceous glands.

Several methods have heretofore been used to collect and quantify the secretions from sebaceous glands. In one such method, a test area on the skin surface is irrigated with a suitable lipid solvent. In another, an absorbent material such as a cigarette paper or cotton is applied on the skin surface for a specified period of time. Subsequent applications of well-known techniques such as chromotography, solvent extraction and distillation permit quantification of the amount of sebum collected. However, these techniques involve pooling of the sebum output and do not provide information regarding the relative concentration or output of sebaceous glands in different skin areas. Another recently introduced method involves absorbing sebum onto a frosted glass plate and then electronically measuring the change in light scattering.

The present invention, however, provides a more satisfactory means for analyzing sebum output at different skin sites in that it involves the use of a comfortable film that, in one application, can provide, in seconds, a convenient broad evaluation of the degree of sebaceous gland activity, and, in another application, can be preserved as a permanent record and used for semi-quantitative estimation without resort to expensive instrumentation or complicated analysis. This permits more rapid diagnosis as well as more focused treatment. In fact, in one aspect of the invention, the same type of device as is used for diagnosis can also be applied to the skin, with or without an active ingredient incorporated therein, and used to treat or prevent outbreaks of acne or other conditions associated with production (or secretion) of sebum by sebaceous glands.

In U.S. Pat. No. 3,449,080, issued June 10, 1969, there is described a diagnostic device for determining the level of chloride in the body sweat of subjects, which device comprises a bibulous paper impregnated with a weakly acid or weakly basic ion exchange resin and a suitable pH indicator such as phenolphthalein. The device is applied to the forehead of a subject, such as a perspiring child. When the device changes color upon being wetted with the subject's perspiration, it is removed and the color compared to a previously prepared color comparison chart. A similar device is described in U.S. Pat. No. 3,552,929, issued Jan. 5, 1971. In this device, there are a plurality of distinct regions which contain different, predetermined amounts of halide-sensitive reagent. A related device is shown in U.S. Pat. No. 4,163,039, issued July 31, 1979, this device being designed to have the impregnated indicator show a color change only when the concentration of sodium or chloride ion in a subject's sweat is at least 50 meq/l. This device also comprises a perforated transparent envelope through which the sweat is absorbed.

These devices, while having some similarity to that of the present invention, are not suitable for the purposes thereof since they depend on color change caused by an ionic reaction, whereas such ionic content as may be present in sebum is essentially irrelevant to the diagnostic purpose of the present invention. Moreover, these references fail to disclose or suggest either the presence or function of the microporous film of the present invention, or the need, when preparing the adhesive coated film of the invention, to provide a coating of adhesive that will not itself migrate into the pores of the microporous film but that permits the passage of sebum therethrough so that the sebum is absorbed into the pores of the film.

DISCLOSURE OF THE INVENTION

In accordance with one aspect of the present invention, there are provided means for collecting sebum secreted from sebaceous glands of a subject in a manner which both discloses the relative location of the active sebaceous glands on the subject's skin and provides a semi-quantitative measure of the relative sebum output of said glands for a given period of time, said means comprising an open-celled, microporous, hydrophobic polymeric film substrate for application to the skin. The film has coated thereon a thin layer of synthetic, pressure-sensitive adhesive consisting essentially of high-molecular weight polymers, this adhesive layer being thick enough to afford suitable adhesion between the microporous substrate and the skin of the subject so as to promote migration of the secreted sebum into the pores of the backing, and thin enough so as not to prevent migration of substantial quantities of sebum therethrough by virtue of its mass. The adhesive must also be substantially incapable of itself migrating into the pores of the polymeric film.

In another aspect, the present invention provides a method for mapping the location of sebaceous glands on the skin, particularly the face of a subject, And of estimating semi-quantitatively the relative sebum output or secretion of said glands per unit of time, said method comprising applying to the skin of a subject for a predetermined period of time an open-celled, microporous, hydrophobic polymeric film, said film preferably having coated on a major surface thereof a layer of synthetic, pressure-sensitive adhesive consisting essentially of high molecular weight polymers, removing said film from said skin after said predetermined time period has passed, and comparing the number and size of translucent areas on the test sample with those on preselected standards. Further, if desired, the sebum can be recovered from the film and the amount and composition thereof determined by known, conventional analytical means.

More particularly, for a rapid, general evaluation of a skin site, the film is applied directly to the skin for a few seconds and compared to a standard. Where more detailed evaluation or a relatively permanent record is desired, the adhesive side of the coated film is applied to the skin for a longer period of time, generally of the order of an hour.

In yet another embodiment of the present invention, the above described microporous film is used therapeutically to control the level of sebum on the skin of a subject by periodic application of the film to the skin in order to remove exess sebum secreted thereon. In a further embodiment, affirmative localized therapy is provided to selected sites of abnormally high (or low) sebum production by first using the above described diagnostic method to ascertain the location of said sites, and then applying to said sites a microporous film impregnated with an active ingredient for controlling sebum secretion from the sebaceous glands at said sites whereby to continuously supply said sebaceous glands with said sebum secretion controlling ingredient.

BEST MODE FOR CARRYING OUT THE INVENTION

A presently preferred open-celled microporous film for use in accordance with the present invention is a microporous polypropylene such as that commercially available from Celanese Fibers Marketing Company under the trademark CELGARD. A particularly preferred film is CELGARD grade 2400. Other such materials can be substituted therefor, however, provided they possess similar necessary qualities, vis: they must be open-celled, microporous materials that are essentially hydrophobic (sweat absorption would interfere with the visualization of sebaceous gland distribution and sebum secretion) and have the capacity to freely absorb such lipids as sebum. Suitable examples include nonwoven materials comprising fibers selected from the group consisting of polyester, polyether and polyolefin fibers, for example, nonwoven pulp sheets impregnated with polyethlene.

In addition to the foregoing qualities, suitable films should have pores of such size and distribution that the film is opaque or opalescent when the pores are empty or filled with air or another gaseous material but become translucent or transparent upon absorption of a lipid such as sebum. For example, a CELGARD microporous polypropylene film that has a pore volume of about 40% and a thickness of about 0.01 to 0.03 mm has been found suitable. Generally, these characteristics are present when the film has a pore volume of from about 25% to about 50% and a film thickness of from about 0.01 mm to about 0.05 mm. Preferably, the effective pore diameters should be less than about 0.1 micron.

While many commercially available pressure-sensitive adhesives can be used to coat the microporous film, it is important that they be virtually without low molecular weight components so as to minimize the possibility of the adhesive migrating into the pores of the microporous film during storage, thereby reducing the opacity of the film. Many conventional pressure sensitive adhesives satisfy these criteria. Preferred adhesives for use in the construction of the present invention are the homopolymers and interpolymers derived from monomers selected from the $C_2$ to $C_{10}$ aliphatic esters of acrylic and methacrylic acid, $C_2$ to $C_{10}$ aliphatic vinyl ethers and esters, acrylamides, urethanes and the like. (Rubber based adhesives and other adhesives containing low molecular weight portions should be avoided as they tend to migrate into the micropores of the film). A terpolymer of 2-ethylehexyl acrylate, vinyl acetate and tert.-butyl acrylamide has been found to be particularly suitable. One such suitable terpolymer has the foregoing monomeric components present in approximate ratios of 60:25:15

As will be appreciated, the adhesive should be applied to the film in such a manner as to provide as uniform a coating as possible. In order to minimize the possibility of the adhesive migrating into the pores of the film, it is preferred that the adhesive be applied by the well-known technique of transfer-coating. For example, the foregoing terpolymer adhesive may be so coated onto the film by first coating a 45% solution therof in ethyl acetate onto a silicone-treated paper to yield a dry coated weight of about 30 to 40 gm per square meter. Thereafter, the dried adhesive is transferred to the microporous film by cold lamination at a pressure of 1.5 to 2.5 MPa (megapascals). The silicone paper can then be stripped away, leaving the adhesive layer transferred to the microporous film. If desired, the silicone paper may be left in place as a release paper for convenience during storage. While coating weights may vary widely, depending on the adhesive used, for example between about 15 and about 60 gm per square meter, coating weights of between about 15 and about 30 gm per square meter are preferred. As already indicated, the thickness of the adhesive coating is not critical, so long as it is not so thick as to interfere with migration of the sebum into the pores of the film overlaying the sebaceous glands nor too thin to provide effective adhesive contact between the film and the skin surface.

When it is only desired to obtain a general evaluation of the degree of sebaceous gland activity, for example, when determining skin type for preliminary clinical evaluation or for selecting suitable skin care products such as for cosmetic use, the microporous film is applied directly to the skin (either uncoated with adhesive or with the adhesive coated side away from the skin area to be tested) for a perio of from about 5 seconds to about 60 seconds, preferably at least about 15 seconds, more preferably about 20 to 30 seconds. This provides a surface impression of greater translucency in the areas of greater sebaceous activity. Oily skins will resullt in a more translucent film than will dry skins, for the same exposure time. The film sample thus obtained tends to lose its translucency after a relatively short period of time, probably because the relative amount of sebum absorbed is small and it tends to diffuse uniformly throughout the pores of the film. It is therefore not suitable for detailed studies or relatively permanent records.

On the other hand, accurate, relatively permanent records of sebaceous activity of skin sites are obtained when the adhesive coated device of the invention is applied to the skin site, with the adhesive coated side in contact with the skin, for periods of from about 20 minutes to about 3 hours, preferably at least about 30 minutes, more preferably about 60 to 90 minutes. It is believed that the greater accuracy and pemanance of the samples thus obtained is because greater relative volumes of sebum are absorbed into, and retained substantially immobile in, the micropores of the coated film.

In either aspect, in order to promote uniformity of results, it is preferable to clean the skin site with a suitable solvent about 5 minutes before applying the film. Without such a pre-cleaning, the results may be obscured by the presence of accumulated sebum on the skin surface, particularly in the case of subjects with oily skin conditions.

The following examples are presented to further illustrate specific embodiments of the present invention.

EXAMPLE 1

About 50 ml of adhesive solution (45% solution of a 60:25:15 terpolymer of 2-ethylhexyl acrylate, vinyl acetate and tert.-butyl acrylamide in ethyl acetate) was poured onto one end of a 30 cm by 200 cm sheet of silicone treated release paper (POLY SLICK S). The solution was coated evenly and continuously on the surface of the release paper by spreading with a doktor blade set so as to leave a 0.1 mm gap between the release paper surface and the blade edge. The coating was dried in a forced air oven at 100° C. to completely remove the solvent. After cooling to room temperature, a sheet of microporous polypropylene film (CELGARD 2400) of similar dimensions to the coated release paper was laminated to the first sheet by passing the two between pinch rollers set to apply a pressure of 2MPa. (Laminations were also prepared by hand rolling with sufficient pressure to roll out air bubbles and provide firm, intimate contact between the film and the sheet). The laminate was then cut into 2.5 cm wide strips, and these cut into approximately 8 cm lengths.

The skin of a test subject's forehead was prepared by cleansing with soap and water, then defatted with a gauze pad saturated with hexane. After the skin surface had dried completely, sebum collecting strips were peeled from the release paper and fixed to the skin surface with gentle pressure to assure adequate adhesion. After 3 hours, the strips were removed and the number and size of the cleared areas (each of which occurs precisely over an actively excreting sebaceous gland) were observed. The tape strips are preserved for future comparison by smoothing them out on a nonporous surface such as a glass plate.

EXAMPLE 2

An adhesive strip prepared and applied as in Example 1 was extracted with a small volume of hexane for 10 minutes, then re-extracted for another 10 minutes with fresh hexane. Analysis of the test strip extract yielded 97 micrograms/square cm/3 hr. The sebum excretion rate (SER) of the same test site was determined by direct extraction of the area with hexane according to a well established technique (Strauss & Pochi, J. of Inv. Derm. 36, 293). The determination yielded an SER of 120 micrograms/square cm/3 hr.

Chromatographic analysis of the two extracts indicated nearly identical composition for the two samplings.

Variations of the invention as described above can, of course, be made without departing from the spirit and scope of the present invention.

I claim:

1. A device for collecting sebum as it is secreted from the sebaceous glands of a subject which comprises (a) an open-celled, microporous, hydrophobic polymeric film having coated on a major surface thereof (b) a layer of synthetic, pressure-sensitive adhesive consisting essentially of high molecular weight components that are resistant to migration into the pores of said microporous film, said layer of adhesive being sufficiently thick and continous to hold said microporous film in close proximity with the openings of said sebaceous glands, yet sufficiently thin to permit passage therethrough, and into said pores of said microporous film, of substantially all of the sebum secreted by said glands during a period of contact between said device and said sebaceous glands, said microporous film having a pore volume of from about 25% to about 50%, a film thickness of from about 0.01 mm to about 0.05 mm, the pores of said film having a mean effective diameter of less than about 0.1 micron, and said film being opaque to light or opolescent when its pores are filled with gaseous material but substantially translucent when said pores are filled with sebum or another hydrophobic substance.

2. The device of claim 1 wherein said microporous film has a pore volume of about 40% and a film thickness of from about 0.01 mm to abut 0.03 mm.

3. The device of claim 1 wherein said film is microporous polypropylene.

4. The device of claim 1 wherein said film is a nonwoven material comprising fibers selected from the group consisting of polyester, polyether and polyolefin fibers.

5. The device of claim 3 wherein said adhesive consists essentially of a high molecular weight polymer selected from the group consisting of the homopolymers and heteropolymers of monomers selected from the $C_2$ to $C_{10}$ aliphatic esters of acrylic and methacrylic acid, the $C_2$ to $C_{10}$ aliphatic vinyl ethers and esters, acrylamides and urethanes.

6. The device of claim 5 wherein said heteropolymer is a terpolymer of 2-ethylhexyl acrylate, vinyl acetate and tert.-butyl acrylamide.

7. A method for determining the location and approximate rate of sebum secretion of sebaceous glands of a subject which comprises (a) applying to the skin of said subject for a predetermined time a device which comprises (i) an open-celled, microporous, hydrophobic polymeric film having coated on a major surface thereof (ii) a layer of synthetic, pressure-sensitive adhesive consisting essentially of high molecular weight components that are resistant to migration into the pores of said microporous film, said layer of adhesive being sufficiently thick and continuous to hold said microporous film in close proximity with the openings of said sebaceous glands, yet sufficiently thin to permit passage therethrough, and into said pores of said microporous film, of substantially all of the sebum secreted by said glands during a period of contact between said device and said sebaceous glands, said microporous film having a pore volume of from about 25% to about 50%, a film thickness of from about 0.01 mm to about 0.05 mm, the pores of said film having a mean effective diameter of less than about 0.1 micron, and said film being opaque to light or opalescent when its pores are filled with gaseous material but substantially translucent when said pores are filled with sebum or another hydrophobic substance, and (b) removing said device upon the expiration of said time period.

8. The method of claim 7 which further comprises (c) observing the location, number and size of translucent areas on said device.

9. The method of claim 7 which further comprises comparing the number and size of translucent areas on said device with a preselected standard.

10. The method of claim 7 which further comprises recovering said sebum from said device and determining the amount of said recovered sebum.

11. The method of claim 7 which further comprises recovering said sebum from said device and determining the composition of said recovered sebum.

12. The method of claim 7 wherein said predetermined time is in the range of from about 20 minutes to about 3 hours.

13. The method of claim 12 wherein said predetermined time is in the range of from about 30 minutes to about 90 minutes.

14. The method of claim 12 wherein said time is at least about 30 minutes.

15. A method for removing excess sebum from the skin of a subject which comprises periodically, sequentially applying thereto and thereafter removing therefrom a device which comprises (a) an open-celled, microporous, hydrophobic polymeric film having coated on a major surface thereof (b) a layer of synthetic, pressure-sensitive adhesive consisting essentially of high molecular weight components that are resistant to migration into the pores of said microporous film, said layer of adhesive being sufficiently thick and continous to hold said microporous film in close proximity with the openings of said sebaceous glands, yet sufficiently thin to permit passage therethrough, and into said pores of said microporous film, of substantially all of the sebum secreted by said glands during a period of contact between said device and said sebaceous glands, said microporous film having a pore volume of from about 25% to about 50%, a film thickness of from about 0.01 mm to about 0.05 mm, the pores of said film having a mean effective diameter of less than about 0.1 micron, and said film being opaque to light or opalescent when its pores are filled with gaseous material but substantially translucent when said pores are filled with sebum or another hydrophobic substance.

* * * * *